United States Patent [19]

Moja et al.

[11] Patent Number: 4,638,013

[45] Date of Patent: Jan. 20, 1987

[54] DIETETIC SUPPLEMENT AND PREPACKAGED FOOD IN WHICH IT IS CONTAINED, PROCESS OF PREPARATION AND METHOD OF ADMINISTRATION

[75] Inventors: Egidio A. Moja, Milan; Gianluigi Gessa, Cagliari, both of Italy

[73] Assignee: Boehringer Biochemia Robin S.p.A., Italy

[21] Appl. No.: 674,853

[22] Filed: Nov. 26, 1984

[30] Foreign Application Priority Data

Nov. 30, 1983 [IT] Italy ................................ 23959 A/83

[51] Int. Cl.⁴ .......................................... A61K 31/195
[52] U.S. Cl. ..................................................... 514/561
[58] Field of Search ............................................ 514/561

[56] References Cited

U.S. PATENT DOCUMENTS 4,279,917 7/1981 Takami et al. ...................... 514/561
4,368,204 1/1983 Sato et al. ............................ 514/561

Primary Examiner—Stanley J. Friedman
Attorney, Agent, or Firm—Bacon & Thomas

[57] ABSTRACT

A completely tryptophan-free dietetic supplement based on amino acids, which has an effect on sleep, comprising at least L-isoleucine (4–16%), L-leucine (9–27%), L-lysine (7–20%), L-methionine (9–27%), L-phenylalanine (9–27%), L-threonine 4–12%) and L-valine (6–19%). It can also comprise other amino acids and substances which contribute calories, minerals and vitamins, as well as the vehicles required by the form of presentation provided for. It can be included in prepackaged foods for meals, for instance normocaloric meals and for infusions.

8 Claims, No Drawings

DIETETIC SUPPLEMENT AND PREPACKAGED FOOD IN WHICH IT IS CONTAINED, PROCESS OF PREPARATION AND METHOD OF ADMINISTRATION

The dietetic supplement refers to a dietetic supplement based on amino acids, which has an effect on sleep, and to a prepackaged food in which it is contained. Said invention also refers to the method of preparation and administration.

For a better understanding of this invention and its inherent problems, the description of said invention is preceded by some brief remarks on the characteristics of human sleep and some of its regulatory biochemical mechanism.

Nowadays it is possible to make a polygraphic study of human sleep. This methodology consists in simultaneous study of the electroencephalogram (EEG), the electromyogram (EMG) and the electro-oculogram (EDG), obtained by attaching electrodes to exact points on the head and permits the entire sleep cycle to be differentiated into consecutive stages. Two main periods can be distinguished: "non-REM" sleep (in which the eyes are still or move slowly) and "REM" sleep (in which the eyes move rapidly and dreams occur). The non-REM period of sleep can, in turn, be differentiated into four stages (stage 1, 2, 3 and 4), characterized by a progressive slowing down of the EEG and increasingly deeper sleep. Stage 4 is the deepest and most restorative. The stages described for an adult human are of somewhat constant average duration with the REM stage taking up 20% of sleep, stages 1 and 2 (light sleep) 55% and stages 3 and 4 (deep sleep) 25%.

Thorough research has been carried out on biochemical mechanisms in the brain, which regulate the alternation and duration of the individual stages of sleep, and on the effects of chemical compounds on these regulatory mechanisms.

In particular, the effect of substances introduced into the organism through food has been studied. Thus, for example, some authors (Lacey J. H. et al. Electroencephl. Clin. Neurophysiol. 44, 275, 1978) have studied the effect on sleep of specific nutrients, like amino acids, the main aim being to correlate variations in calories introduced in this way with specific variations in the individual stages of sleep. It should be especially noted that non research appears to have been done into the effect on sleep of selective deprivation of a single amino acid by not including it in the protein substances administered, whereas it has been discovered that completely stopping administration of food leads to an increase in slow sleep (McFadyen U. M. et al.: J. Appl. Physiol., 35, 391, 1973). The action of serotonin, which is present in the brain of humans and mammals, has been the object of special study. The human organism is not able to synthesize this substance directly, but only by using tryptophan as substrate. As is known, the latter is an essential amino acid present in many proteins which are ingested into the human organism in food and small quantities of it are found in the brain.

There are two different theories about the role played by serotonin in regulating sleep. According to one (Jouvet M., Science 163: 32, 1969) a reduction in non-REM sleep is a consequence of the reduction of levels of serotonin in the brain.

On the contrary, Wyatt and Mendelson (Biol. Psychiatry, 5/33, 1972 and Mendelson et al., Biol. Psychiatry 10: 459, 1972) have demonstrated that drugs able to block synthesis and activity of serotonin, such as p-chlorophenylalanine and methysergide, reduce REM sleep in humans.

Thus, other researchers have studied the effects on human sleep of tryptophan, the biochemical precursor in the synthesis of serotonin.

H. Hartmann et al. (Psychopharmacology 19, 114, 1971) report that the administration of tryptophan reduces sleep latency time, whereas Wyatt et al. (Lancet, II, 842, 1970) report that deep sleep is induced by administration of tryptophan. Then, however, Hartmann and Spinweber (Y. New Mental Diseases 167, 497, 1979) record that such an increase in slow sleep only occurs after ingestion of limited quantities of tryptophan (0.25 g), but not after larger quantities, such as 0.5 and 1 g. It is clear that the results of the above-mentioned exp riments do not coincide with one another, neither to they allow definitive conclusions to be drawn about the effects of serotonin and tryptophan on human sleep. In particular, data are lacking about the effects on the nature and duration of sleep of administering totally tryptophan-free amino acid mixtures.

This is especially important after Gessa et al. (J. Neuroché., 22, 869, 1974; Biggio et al., Life Sci., 14: 1321, 1974) have shown that administering of particular diets of essential amino acids, totally tryptophan-free, to rats reduces the level and activity of serotonin in the brain.

This can be explained by the fact that, as tryptophan is not included in the food, the brain is deprived of this substance, where it acts as a biosynthetic precursor of serotonin. Consequently, the synthesis of serotonin in the brain is reduced.

Subsequently, Moja et Al. (Sci., 24: 1467, 1979) have shown that, following administration of tryptophan-free essential amino acid diets to rats, there was a significant reduction in REM sleep.

On the other hand, Concu et al. (IRCS Medical Science 5, 520, 1977) report that the administration of a tryptophan-free diet to humans is less effective in reducing a state of anxiety than a diet containing all amino acids.

Surprisingly and unexpectedly it has now been discovered that the administration to humans of completely tryptophan-free mixtures of amino acids determines a significant increase in the percentage of stage 4 sleep, namely the stage of deepest sleep, which is especially restorative without significant reduction in light and REM sleep.

Therefore, the object of the present invention is, in particular, a dietetic supplement based on amino acids, characterized in that it is entirely tryptophan-free and is formulated, in terms of quality and quantity, in such a way as to act specifically on stage 4 sleep in humans, increasing the percentage of said sleep.

Its composition cannot be compared in any way with other known formulas which are useful for therapy and contain amino acids, in as much as it is specifically formulated for intervening expressly in human sleep and the fourth stage in particular, of which it increases the percentage.

The dietetic supplement according to this invention should contain at least the following amino acids: L-isoleucine, L-leucine, L-lysine, L-methionine, L-phenylalanine, L-threonine and L-valine.

A preferred composition has been found which is useful for inducing the best effects on stage 4 sleep. This composition of the various above-mentioned amino acids, expressed percentage-wise in grams, i.e. per 100 g of the total amino acid content in the dietetic supplement, corresponds to: L-isoleucine (11,4 g); L-leucine (18 g); L-lysine (13.2 g); L-methionine (18 g); L-phenylalanine (18 g); L-threonine (8.2 g) and L-valine (13.2 g).

Nevertheless, it has been found that a totally satisfactory effect on stage 4 sleep can also be achieved by using mixtures of said amino acids, in which the percentage of one or more of the single amino acids are increased or reduced by 50% compared to the preferred percentages. Therefore, the variability limits of the single amino acids in the mixture lie between 4 and 16% for L-isoleucine, 9 and 27% for L-leucine, L-methionine and L-phenylalanine, 7 and 20% for L-lysine, 4 and 12% for L-threonine and 6 and 19% for L-valine.

The dose to be administered and the number of administrations will vary as a function of the patient's age, state of health, weight and seriousness of the illness. Said dose is between 6 and 25 g of dietetic supplement, the preferred amount for administration being between 12 and 15 g.

Other substances can be added to the dietetic supplement according to the present invention for improving its organoleptic, dietetic and therapeutic properties, as well as giving it the envisaged form of presentation, provided said substances are completely trytophan-free.

Object of the present invention are also some variants of the above-mentioned formula, which are able to meet particular requirements, such as those of a hypercaloric diet, a normocaloric diet, a hypocaloric diet and a diet which also includes, for example, vitamins, minerals and other non-essential amino acids, as can be seen in the examples given below.

In particular, vitamins which can be included in the formula are, for example, A, C, D and the B-group vitamins; amino acids, for example, cystine, arginine and histidine; minerals, especially those containing phosphorus, iron, calcium and potassium, compatible with the use envisaged for the present formula.

As far as regards the method of administering the dietetic supplement according to the present invention, it should be kept in mind that food and drink, usually taken during the course of day with a normal diet, contains proteins of vegetable and animal origin, more or less rich in tryptophan. It is therefore obvious that patients suffering from insomnia, who wish to have the full beneficial effect of the dietetic supplement claimed in this patent, especially on the deepest stage 4 of sleep, should preferably abstain from the food and drink of a normal diet which could supply even large quantities of tryptophan and thus interfere with the action of the dietetic supplement claimed in this patent, by lowering the specific action required.

The optional period of abstinence from food and drink potentially rich in tryptophan varies from subject to subject as a function of age, weight and degree of lack of stage 4 sleep.

On the other hand, the particular composition formulated for the dietetic supplement of the present invention in its different proposed versions may be a remedy to a necessary prolonged abstinence from normal food and drink.

Thus, object of the present invention are also dietetic supplements which provide for the addition to the basic formula of other amino acids, glucides, lipids, vitamins, mineral salts and flavours, so as to provide a particular diet, provided for in the different cases of administration, for example, a normocaloric diet, a hypocaloric diet (for example, a sweetener containing fructose, saccharin or aspartame), a hypercaloric diet (using saccharose as sweetener) or even a diet enriched with vitaminis, oligoelements or other dietetic substances.

The substances added may be different solid or liquid vehicles, like water or other diluents, binders, edulcorants and other, provided they are inert with regard to the specific activity envisaged for the final product. Thus, the final product may be, for example, in the form of an aqueous solution, a concentrate for diluting, a powder or granules.

Object of the present invention are also, especially, prepackaged foods for meals, for instance for monocaloric meals, which contain the dietetic supplement claimed in this patent and thereby allow for a tryptophan-free normocaloric diet, as a substitute for the usual diet. Said prepackaged foods are presented in granular form or as a solution for infusion.

The process of preparing the dietetic supplement according to the present invention essentially requires that the final product is guaranteed to be tryptophan-free, in as much as the exogenous presence of said substance, even in small quantities, could—as is already known—reduce the degree of the required effect, i.e. prolonging of stage 4 sleep. As is well-known, tryptophan is found in most animal proteins, for example in milk proteins and vegetable proteins, for example soya, normally used in food products.

Nevertheless, protein hydrolysates from these proteins, like other protein hydrolysates, and the single amino acids, obtained from protein hydrolysates, could be conveniently used in the preparation of the dietetic supplement, object of the present invention, provided that it is ensured they are totally tryptophan-free.

The process of purifying from tryptophan through chromatographic separation, which could permit separation of tryptophan from the other components in the mixture, is too difficult and costly for an industrial process.

As an alternative to cromatographic purification, recourse can be had to a process of enzymatic purification from tryptofano by treating a protein hydrolysate with a tryptophanase, for example, the tryptophanase obtained from purified culture of *Escherichia Coli*, as described by R. O. Burns and R. O. Moss (Bioch. Biopys Acta 65, 233, 1962).

For this purpose the protein hydrolysate, containing the amino acids to be purified, is subjected to enzymatic treatment with a purified tryptophanase at a temperature of 20° C. for 6 to 12 hours, said treatment being carried out in stainless steel containers. The tryptophanase must be found in the hydrolysate at a ratio of about between 1:1,000 and 1:10,000.

Animal protein, like milk protein, or vegetable protein, like soya protein, can be used for the protein hydrolysate. The mass, originating from the enzymatic action, is completely tryptophan-free after this treatment. Said mass can be obtionally then filtered through diatomite and the protein lysate, obtained in this way, is concentrated and evaporated in a dry vacuum. With this process an amino-acid yield of between 95 and 98% is obtained.

Finally, the absence of tryptophan is checked by subjecting the mixture obtained in this way to chromatographic analysis, for example, in a Beckmann type amino-acid analyzer and, if necessary, said mixture is supplemented with the essential amino acids, listed above in the basic formula, which may be missing from it.

Preliminary purification with tryptophanase, by using the above described method, will also be appropriate, if single amino acids and/or their mixtures are used, which originate from enrichment or purification of protein hydrolysates.

A preferred variant for the preparation of the dietetic supplement, object of the present invention, is the mixing of L-amino acids of synthesis, which are found on the market in the most pure state, the degree of purity being, in any case, ascertained from the chromatographic analysis data.

The amino acids mixing techniques, which provide the dietetic supplement, like those for mixing said dietetic supplement with other optional ingredients which have previously been checked for absence of tryptophan, are the usual ones adopted in pharmaceutical practice, known to the experts in this field. As described above, the final product will be provided, for example, in single-dose forms of an acqueous solution, a concentrate for diluting, a powder, granules, tablets and effervescent tablets, by using conventional diluents and excipients, provided they are tryptophan-free.

Conventional excipients and diluents are, for example water, lactose, dextrose, saccharose, mannitol, sorbitol, cellulose and its derivates like for instance carboxymethyl cellulose, talc, stearic acid, calcium and magnesium stearate, glycol, starch, alginic acid and alginates, polysorbates, vegetable oils and zein.

For practical application, the usefulness and advantages offered by the present invention can be summarized as follows:

possibility of increasing the percentage of sleep in stage 4, namely restorative sleep, during a normal number of hours of sleep;

possibility of attaining a normal duration of stage 4, namely restorative sleep, even though reducing the number of hours of sleep, when such a reduction is required for various necessities;

complete atoxicity of the product, which determines the required therapeutic effect by inducing a dietetic lack of tryptophan, without at the same time introducing foreign or, at any rate, potentially harmful substances into the organism;

possibility of being adapted to the different requirements or individuals.

The following examples illustrate, but are not binding on the present invention.

EXAMPLE 1

Twelve healthy volunteers, aged between 18 and 48, were used in the experiment. Each subject was made to sleep in the sleep laboratory, equipped for polygraphic recording, for three consecutive nights. The first night was for adaptation. On nights two and three each subject received two different dietetic supplements, defined as tryptophan-free diet and control diet respectively. The tryptophan-free diet was composed as follows: L-isoleucine (1.4 g), L-leucine (2.2 g), L-lysine (1.6 g), L-methionine (2.2 g), L-phenylalanine (2.2 g), L-threonine (1.0 g), L-valine (1.6 g) and saccharose (10.0 g).

The control diet differed from the former by the addition of 0.5 g of tryptophan.

On each night the subjects received just one of the two dietetic supplements mentioned above and the sequence for administering the two supplements was randomized.

During the ten hours preceding administration of the dietetic supplement the subjects were only allowed to ingest water.

The polygraphic tracings were analyzed by a researcher who was blind with regard to the diet adopted, according to the internationally accepted technique (Rechtscheffen A. and Kales A., P.H.S., U.S. Government Printing Office, Washington D.C., 1968), which provides for subdivision of the sleep period into the previously described stages 1, 2, 3, 4 and REM.

The results for the first three hours of sleep are collected together in the table below, which gives the different sleep parameters relative to the nights with complete diet and tryptophan-free diet respectively.

TABLE

EEG SLEEP CHARACTERISTICS AFTER A TRYPTOPHAN-FREE DIET IN 12 VOLUNTEERS. DATA FOR THE FIRST THREE HOURS OF RECORDING.

|  | Control diet containing tryptophan | Tryptophan-free diet | Significance of difference (*) |
|---|---|---|---|
| Sleep latency | 14.0 (±13.9) | 14.4 (±14.4) | |
| Total sleep time (min) (T.S.T.) | 155.4 (±28.7) | 151.3 (28.2) | |
| Stage 1 (min) | 14.2 (±11.2) | 10.0 (±5.1) | |
| (% T.S.T.) | 11.8 (±16.8) | 7.0 (±3.8) | |
| Stage 2 (min) | 81.4 (±25.6) | 68.0 (±30.9) | |
| (% T.S.T.) | 51.2 (±10.3) | 44.4 (±16.4) | |
| Stage 3 (min) | 13.2 (±7.3) | 14.3 (±8.3) | |
| (% T.S.T.) | 8.2 (±4.3) | 9.6 (±5.3) | |
| Stage 4 (min) | 23.7 (±20.3) | 40.8 (±26.4) | $p < 0.02$ |
| (% T.S.T.) | 14.9 (±12.2) | 28.3 (±17.2) | $p < 0.01$ |
| Stage REM (min) | 23.0 (±16.4) | 17.2 (±12.6) | |
| (% T.S.T.) | 13.9 (±9.5) | 10.1 (±8.3) | |
| Stage 3 latency (min) | 40.5 (±34.7) | 26.2 (±15.7) | |
| Stage 4 latency (min) | 53.9 (±38.1) | 32.7 (±21.2) | $p < 0.05$ |
| Stage REM latency (min) | 88.4 (±43.3) | 108.4 (±81.6) | |
| Waking during sleep (min) | 8.6 (±16.6) | 9.8 (±15.9) | |
| (number of times) | 2.2 (±2.8) | 2.0 (±1.9) | |

All values represent mean (± S.D.) (standard deviation)
(*)Statistical method for paired data, two-tailed, 11 degrees of liberty The first column in the table gives the parameters studied, namely: sleep latency (difference in minutes between start of recording and the first ten consecutive minutes of sleep), percentage of total sleep time in the different stages (1, 2, 3, 4 and REM), latency of stages 3, 4 and REM and duration and number of wakings during sleep. The data in the column are the averages ± the standard deviation of the twelve volunteers studied, relative to the times when the dietetic supplement containing all the amino acids (including tryptophan) was administered. The third column gives analogous data for the dietetic supplement (tryptophan-free). The fourth column shows the statistical significance of the differences between the data, that is, the differences between the two data groups (with and without tryptophan) were analysed sing Student's "t" method for paired data (a statistical test for comparing averages).

Significance is established at p (probability)<0.05, that is, the probability that the difference obtained is random and less than 1 out of 20.

It appears from the table that administration of a tryptophan-free mixture to humans produces a significant increase in stage 4 and a non-significant compensatory reduction in light and REM sleep.

EXAMPLE 2

Under experimental conditions according to the procedure in Example 1 the addition of other amino acids to the diet, like, for example, glycine or alanine, and the doubling per subject of the amount of tryptophan-free essential amino acids ingested intensify the effect of lack of tryptophan by further increasing the percentage of stage 4 sleep.

EXAMPLE 3

A formulation of essential amino acids suitable for increasing percentage wise the duration of stage 4 sleep, in which, according to Example 1, the total content of amino acids of 12.2 g consists of: L-isoleucine (1.4 ); L-leucine (2.2 g); L-lysine (1.6 g); L-methionine (2.2 g); L-threonine (1.0 g) and L-valine (1.6 g).

EXAMPLE 4

A formulation according to Example 1, consisting of the formulation in Example 3 with the addition of 10 g of saccharose, it supplies a dietetic supplement rich in calories.

EXAMPLE 5

A hypocaloric dietetic supplement is obtained by adding 1 g of fructose to the formula in Example 3.

EXAMPLE 6

A dietetic supplement enriched with mineral salts is obtained by supplementing the composition in Example 3 with 0.25 g of calcium phosphate, 0.100 g of iron sulphate and 0.100 g of potassium chloride.

EXAMPLE 7

A composition is prepared enriched with vitamins and amino acids according to the following formula:

L-isoleucine (1.0 g); L-leucine (2.4 g); L-lysine (1.5 g); L-methionine (1.4 g); L-phenylalanine (2.0 g); L-threonine (1.4 g); L-valine (1.5 g); L-cystine (0.2 g); vitamin A 5000 I.U.; vitamin B1 (1.6 mg); vitamin B12 (2.5 mg); vitamin PP (18 mg); vitamin B6 (2.4 mg) and vitamin C (100 g).

EXAMPLE 8

A dietetic supplement enriched with amino acids and mineral salts is obtained with the following formula:

L-isoleucine (2 g); L-leucine (1.8 g); L-lysine 1.3 ); L-methionine (1.76 g); L-methylalanine (2.5 g); L-threonine (1.4 g); L-valine (1.5 g); suitable salts containing calcium (1 g); phosphorus (0.8 g) and iron (15 g).

EXAMPLE 9

A prepackage food, which contains the dietetic supplement of the present invention, is prepared by mixing under dry conditions in suitable receivers the amino acids, malt, dextrine, fructose, soya lecithin, hydrogenated food fats and 50% of saccharose and purified water, until blended.

The blended mixture is then granulated under humid conditions and dried in a fluid bed. The granules obtained in this way are then further screened to the required size and all the other components are added for mixing under dry conditions. The end item in the form of easily dispersible granules is then subdivided into single-doses with the following average composition:

| | | | | |
|---|---|---|---|---|
| 25. L-Leucine | 2.2 g | Vitamin B | 0.55 | mg |
| L-isoleucine | 1.4 g | Vitamin PP | 10 | mg |
| L-lysine HCl | 2.0 g | Vitamin C | 23 | mg |
| L-methionine | 2.2 g | Vitamin $D_2$ | 164 | U.I. |
| L-threonine | 1.0 g | Vitamin E | 12 | U.I. |
| 5. l-valine | 1.6 g | Folic acid | 154 | mcg |
| L-phenylalanine | 2.2 g | Pantothenic acid | 3.3 | mg |
| Malt dextrine | 110.0 g | Calcium | 250 | mg |
| Saccharose | 40.0 g | Phosphorus | 206 | mg |
| Fructose | 10.0 g | Iron | 7.3 | mg |
| 10. Dextrose | 20.0 g | Magnesium | 65 | mg |
| Soya lecithin | 4.0 g | Copper | 0.75 | mg |
| Hydrogenated food fats | 12.0 g | Zinc | 5.45 | mg |
| Vitamin A | 1788 U.I. | Potassium | 258 | mg |
| Vitamin $B_6$ | 0.75 mg | Iodine | 60 | mcg |
| 15. Vitamin $B_{12}$ | 1.75 mcg | Manganese | 1.2 | mg |
| Vitamin $B_2$ | 0.36 mg | Sodium | 82 | mg |
| Natural flavours q.b. | | | | |

When used it can be diluted in about 300 ml of cold or likewarm water, thereby obtaining a food in the form of a liquid (milk-shake). If, on the other hand, 4 g of carrageen are added to the above-mentioned formula and it is diluted with water, a semisolid food is obtained (pudding).

In both cases the contribution of calories in such a formula corresponds to about 940 Kcal and, therefore, to the amount generally ingested from a normal meal.

EXAMPLE 10

A dietetic supplement in the form of solutions for infusion (for use in hospitals), which can facilitate induction and prolongation of stage 4 sleep, is presented in two ampoules, containing the compositions indicated below, corresponding to a preferred formula.

They are provided for simultaneous administration at moment of use.

| Ampoule A (500 ml) | |
|---|---|
| L-isoleucine | 4.500 g |
| L-leucine | 5.500 g |
| L-lysine HCl | 3.800 g |
| L-methionine | 0.500 g |
| L-phenylalanine | 0.500 g |
| L-threonine | 2.250 g |
| L-valine | 4.200 g |
| L-arginine | 3.000 g |
| L-histidine | 1.200 g |
| Glycine | 4.500 g |
| L-serine | 2.500 g |
| L-alanine | 3.750 g |
| L-proline | 4.000 g |
| Sodium edetate | 0.025 g |
| Sodium metabisulphate | 0.400 g |
| Hydrochloric acid 37% | 2.800 g |
| Inj. distilled water q.b. at 500 ml | |

| Ampoule B (500 ml) | |
|---|---|
| Injectable glucose | 253.000 g |
| Calcium chloride | 0.294 g |
| Magnesium chloride | 0.508 g |
| Sodium chloride | 0.584 g |
| Sodium glycerophosphate | 3.060 g |
| Acetic acid | 0.540 g |
| Sodium hydrate drops | 0.280 g |
| Sodium metabisulphate | 0.200 g |
| Inj. distilled water q.b. at 500 ml | |

In preparing the single infusion-type solutions all the components are dissolved in distilled apyrogenic water and the preparation is brought to the required volume. The solution obtained is filtered through an absolute filter (0.2μ), bottled and sterilized at 121° C. for 20 minutes.

What we claim is:

1. A method for prolonging stage 4 sleep in humans which comprises administering to said humans, a tryptophan-free dietetic supplement comprising L-isoleucine, 4–16%; L-leucine, 9–27%; L-lysine, 7–20%; L-methionine, 9–27%; L-phenylalanine, 9–27%; L-threonine, 4–12%, and L-valine, 6–19%.

2. The method of claim 1 which further comprises refraining from eating food containing tryptophan.

3. The method of claim 2 wherein the tryptophan-free dietetic supplement is administered orally or by infusion or by intestinal intubation.

4. The method of claim 2 wherein the tryptophan-free dietetic supplement comprises L-leucine, 18%; L-isoleucine, 11.4%; L-lysine, 13.2%; L-methionine, 18%; phenylalanine, 18%; L-threonine, 8.2%; and L-valine, 13.2%.

5. The method of claim 2 wherein the tryptophan-free dietetic supplement is administered in a quantity between 6 g and 25 g in weight.

6. The method of claim 2 wherein the tryptophan-free dietetic supplement additionally contains a non-essential amino acid, a mineral, a vitamin, a preservative, and emulsifier or a flavoring agent.

7. The method of claim 2 wherein the dietetic supplement additionally contains an inert vehicle.

8. The method of claim 2 wherein the dietetic supplement is in the form of a powder, granules, a solution or a concentrate for diluting.

* * * * *